(12) United States Patent
Karlsson

(10) Patent No.: US 9,283,325 B2
(45) Date of Patent: Mar. 15, 2016

(54) MEDICAMENT DELIVERY DEVICE WITH DOSE RE-SETTING

(75) Inventor: Anders Karlsson, Saltsjö-Boo (SE)

(73) Assignee: SHL Group AB, Nacka Strand (SE)

( * ) Notice: Subject to any disclaimer, the term of this patent is extended or adjusted under 35 U.S.C. 154(b) by 117 days.

(21) Appl. No.: 14/116,841

(22) PCT Filed: May 3, 2012

(86) PCT No.: PCT/SE2012/050463
§ 371 (c)(1),
(2), (4) Date: Nov. 11, 2013

(87) PCT Pub. No.: WO2012/154110
PCT Pub. Date: Nov. 15, 2012

(65) Prior Publication Data
US 2014/0088515 A1    Mar. 27, 2014

Related U.S. Application Data

(60) Provisional application No. 61/485,235, filed on May 12, 2011.

(30) Foreign Application Priority Data

May 12, 2011    (SE) ........................ 1150427

(51) Int. Cl.
*A61M 5/315*    (2006.01)
*A61M 5/20*    (2006.01)
*A61M 5/31*    (2006.01)
(52) U.S. Cl.
CPC ............. *A61M 5/31583* (2013.01); *A61M 5/20* (2013.01); *A61M 5/31535* (2013.01); *A61M 5/31553* (2013.01); *A61M 2005/3126* (2013.01)

(58) Field of Classification Search
CPC ............. A61M 5/31583; A61M 5/31553; A61M 5/31535; A61M 5/31548; A61M 5/20; A61M 2005/3126
See application file for complete search history.

(56) References Cited

U.S. PATENT DOCUMENTS 5,626,566 A * 5/1997 Petersen et al. ............... 604/208
5,674,204 A * 10/1997 Chanoch ...................... 604/211
(Continued)

FOREIGN PATENT DOCUMENTS

EP    1218042 B1    2/2006
WO    2011/025448 A1    3/2011

OTHER PUBLICATIONS

Sweden Patent Office, Int'l Search Report in PCT/SE2012/050463, Aug. 27, 2012.
(Continued)

*Primary Examiner* — Andrew Gilbert
(74) *Attorney, Agent, or Firm* — Piedmont Intellectual Property

(57) ABSTRACT

The present invention relates to a medicament delivery device comprising a housing (10,12), capable of containing a medicament container (14), a plunger rod (18) and a drive member (34) arranged to said plunger rod and capable of acting on said plunger rod (18) for moving it in the proximal direction of the device for expelling a dose of medicament from said medicament container (14), a dose and drive setting mechanism (52) comprising a dose setting member (56) operably connected to a force member (82) such that setting of a dose causes said force member (82) to be energized. The intermediate member (68) is configured to interact with a dose setting sleeve (50) through a first unidirectional connection (64, 62), configured to interact with said drive member (34) through a second unidirectional connection (70, 72), and configured to interact with a dose drive sleeve (76) through a third connection (74,78).

20 Claims, 14 Drawing Sheets

(56) References Cited

U.S. PATENT DOCUMENTS

| | | | |
|---|---|---|---|
| 6,004,297 A * | 12/1999 | Steenfeldt-Jensen et al. | 604/207 |
| 7,850,662 B2 * | 12/2010 | Veasey et al. | 604/207 |
| 8,152,766 B2 * | 4/2012 | Karlsson et al. | 604/134 |
| 8,353,878 B2 * | 1/2013 | Moller et al. | 604/207 |
| 8,366,680 B2 * | 2/2013 | Raab | 604/211 |
| 8,617,109 B2 * | 12/2013 | Kronestedt et al. | 604/135 |
| 8,968,258 B2 * | 3/2015 | Nzike et al. | 604/220 |
| 9,011,386 B2 * | 4/2015 | Kronestedt et al. | 604/186 |
| 2001/0051792 A1 * | 12/2001 | Kirchhofer et al. | 604/209 |
| 2002/0007154 A1 * | 1/2002 | Hansen et al. | 604/207 |
| 2004/0210199 A1 * | 10/2004 | Atterbury et al. | 604/224 |
| 2005/0090782 A1 * | 4/2005 | Marshall et al. | 604/211 |
| 2006/0276754 A1 * | 12/2006 | Kronestedt et al. | 604/186 |
| 2007/0129687 A1 * | 6/2007 | Marshall et al. | 604/207 |
| 2008/0147005 A1 | 6/2008 | Moller et al. | |
| 2009/0275914 A1 * | 11/2009 | Harms et al. | 604/506 |
| 2009/0281495 A1 * | 11/2009 | Karlsson et al. | 604/134 |
| 2010/0114025 A1 * | 5/2010 | Moller | 604/135 |
| 2010/0152672 A1 * | 6/2010 | Raab | 604/208 |
| 2010/0186739 A1 * | 7/2010 | Kronestedt et al. | 128/203.12 |
| 2012/0095413 A1 * | 4/2012 | Nzike et al. | 604/211 |
| 2012/0209208 A1 * | 8/2012 | Stefanski | 604/189 |
| 2012/0265151 A1 * | 10/2012 | Nzike et al. | 604/211 |
| 2013/0046247 A1 * | 2/2013 | Nzike et al. | 604/211 |
| 2013/0218128 A1 * | 8/2013 | Cowe | 604/506 |

OTHER PUBLICATIONS

Sweden Patent Office, Written Opinion in PCT/SE2012/050463, Aug. 27, 2012.

* cited by examiner

MEDICAMENT DELIVERY DEVICE WITH DOSE RE-SETTING

TECHNICAL FIELD

The present invention relates to a medicament delivery device and in particular to a device with which a certain dose of medicament to be delivered may be set prior to dose delivery.

BACKGROUND OF THE INVENTION

There are a number of medicament delivery devices on the market that are capable of delivering a certain prescribed dose that has been set by the user before dose delivery. This feature of the medicament delivery devices is practical in many instances because the same type of medicament delivery device may be used for different types of drugs, for patients with different needs and thus for different dose sizes such as for children or for adults and/or for medicament administration schemes that vary over time. Instead of having specific designs delivering certain fixed dose amounts, a certain dose may be set by the patient directly before dose delivery. The feature of setting specific doses is also practical with multi-dose injection devices, which are capable of delivering a number of specified, set, doses until the compartment is empty. One example is disclosed in the European patent application publication EP1218042, where specific doses can be set before injection by turning a dose setting button on the distal end of the injector.

If however a dose is set too high, i.e. the user overshoots the desired dose, the device has to be reset so that a user may set the proper dose. According to EP1218042 this is done by continuing the rotation of the dose setting knob until it is moved past the maximum value, past which the dose setting knob is released. It is then possible to rotate back the dose setting knob to the initial, or zero, position, at which position the dose setting knob is re-connected to the dose setting mechanism.

A clear drawback with the solution according to EP1218042 is that if the dose is overshot, the dose knob has to be rotated the whole way to the end position and then rotated back to the zero position, and then again turned to the desired dose. Thus, if a dose setting is missed a lot of rotation is required in order reset the device and set the dose. Further, the design requires a substantial number of interacting components in order to achieve the desired function.

There is thus room for improvements regarding this type of medicament delivery device.

BRIEF DESCRIPTION OF THE INVENTION

The aim of the present invention is to remedy the drawbacks of the state of the art medicament delivery devices.

The device according to the invention utilizes a dose and drive setting mechanism comprising an intermediate member or component, i. e. a member that may transfer movements and functions between different components that are arranged to set and re-set a dose of medicament as well as components that are arranged to deliver a set dose.

The dose and drive setting mechanism may further comprise a dose setting assembly operably connected to a force member. The components of the dose setting assembly that may be utilized to set and reset a dose may comprise among others a dose setting member comprised in a dose and drive setting mechanism accessible on the device by a user. Preferably the dose setting member may be rotated in a certain direction in relation to the device in order to set a dose and more preferably rotated in a particular direction around a longitudinal axis in order to set a dose. In one embodiment of the invention the dose setting member comprises a dose setting knob located at a distal end of the device. The dose setting assembly may further comprise a dose setting sleeve fixedly connected to said dose setting member, and a dose drive sleeve coaxially arranged on said dose setting sleeve and operably connected to said force member.

The function of the force member is to be energized, where the energy from the force member is utilized to expel a dose of medicament from a medicament container that is contained in the medicament delivery device.

The dose setting assembly may preferably be operably connected to said force member via the intermediate member such that when a dose is set by a user, the force in the force member is increased. The intermediate member may thus be positioned operatively to transform movement from the dose setting member to the force member such that when a dose is set by for example by rotating the dose setting knob in one direction, the force of the force member is increased. According to a preferred solution, the connection between the dose setting sleeve and the intermediate member may constitute a first unidirectional connection.

The first unidirectional connection may be capable of transferring movement from said dose setting member to said force member via said intermediate member in one direction for setting a dose and energizing said force member. The first unidirectional connection may comprise a first ratchet connection. Preferably the first ratchet connection comprises wedge-shaped teeth having a certain inclination $\alpha$ and a certain tooth height $h_1$.

The force member may be a tensioning member such as a spring force member. The spring force member may comprise a constant force spring or a compression affected spring force member which may comprise a spiral compression spring, a plate compression spring for example. More preferably the spring force member may comprise a torsion affected spring means which may comprise a spiral spring means that may be twisted along its longitudinal axis, a wound flat band clock spring as a constant force spring or a variable force spring for example.

The components that may be utilized to deliver a dose may comprise a plunger rod that preferably is arranged to be movable in the longitudinal direction of the device. The plunger rod is preferably positioned such that it may act, when moving, on a stopper arranged movable inside a medicament container, whereby the movement of the stopper may cause a dose of medicament to be delivered from the medicament container. In this context, a suitable dose delivery member may be arranged to the medicament container, through which medicament delivery member the dose of medicament may be expelled.

According to one feasible solution, the plunger rod may be arranged with threads on its outer surface, which threads are designed to cooperate with a drive member. According to one feasible solution, the plunger rod cooperates with stationary fixed threads so that the plunger rod is forced to rotate by the drive member in order to move the plunger rod in the longitudinal direction for acting on the stopper of the medicament container.

According to a preferred solution the plunger rod is arranged to be locked against rotation, but being movable linearly, and that a drive member comprises a drive nut that is forced to rotate by said force member, thereby acting as the plunger rod driver, in order to move the plunger rod in the longitudinal direction for acting on the stopper of the medicament container.

According to the invention, the intermediate member is arranged to cooperate with said force member in order to transfer a torque force to said drive member in order to move said plunger rod for delivering a dose of medicament. According to one preferred embodiment, the drive member is a drive nut where a connection is established between the intermediate member and the drive member. According to one preferred solution, the connection constitutes a second unidirectional connection, which is arranged such that it transforms movement from the force member to the drive member via the intermediate member.

The second unidirectional connection may comprise a second ratchet connection. Preferably the second ratchet connection comprises wedge-shaped teeth having a certain inclination $\beta$ and a certain tooth height $h_2$.

According to one aspect, the second unidirectional connection is arranged to allow relative movement between the intermediate member and the drive member when said intermediate member is moved by said dose setting member for setting a dose and for energizing said force member. Said second unidirectional connection is also arranged to prevent movement of the intermediate member in an opposite direction, thereby holding said force member in the energized state.

According to a particular aspect of the invention, the intermediate member may be positioned operatively to transform movement from the dose setting member to the force member such that when a dose is set by rotating the dose setting member in a second direction the force of the force member is decreased, such as for decreasing the size of a set dose or to reset the whole device. The second direction may be the opposite direction, as to when the force of the force member is increased. The dose setting member may then be used both for increasing the force and setting a dose as well as decreasing the force and resetting a dose.

For this purpose, the first and second unidirectional connections may cooperate such that when the dose setting member is operated in the opposite direction, the first unidirectional connection may be designed and arranged to be able to disconnect said second unidirectional connection. Thereby the intermediate member is free to move, and thereby the force member, whereby the force will be reduced.

According to a preferred solution of the invention, the inclination $\alpha$ of the first ratchet connection may be chosen larger than the inclination $\beta$ of the second ratchet connection. Also the tooth height $h_1$ of the first ratchet connection may be chosen larger than the tooth height $h_2$ of the second ratchet connection.

Thereby, when the dose setting member is rotated in the opposite direction and relative the intermediate member, the teeth of the first ratchet connection will slide on each other, whereby the teeth of the second ratchet connection will be moved out of engagement with each other, because of the lesser height.

According to a preferred solution, the connection between the dose drive sleeve and the intermediate member may constitute a third connection. According to one solution, this third connection enables a relative movement in a longitudinal direction between the intermediate member and the force member. This in turn facilitates the disconnection of the second unidirectional connection by said first unidirectional connection, and in particular when ratchet connections are utilized.

A preferable solution of the third connection may be to utilize wedge-shaped teeth that cooperate with surfaces inclined in relation to the longitudinal direction. By this design, any force from the force member will cause the intermediate member to be forced in a longitudinal direction as well as a rotational direction. The movement in the longitudinal direction may then force the second ratchet connection in re-engagement when the teeth of the first ratchet connection have come to a subsequent meshing position when resetting the dose. Further, the design of the third connection will ascertain a force from the force member on all components, including both first and second unidirectional connections, such that a good and stable contact is obtained in any event.

The device according to the invention may further comprise an activation mechanism that may be operably connected to said drive member for releasing said force member. The activation mechanism may comprise a manually operated activation member accessible on the device. The manually operated activation member may be movable in relation to the housing of the device. The activation member may be a component that is moved when the device is moved in contact with a dose delivery site. This may for example comprise a needle guard or needle shield, when a dose delivery member is an injection needle, which may be positioned at a proximal end of the device. Preferably the activation member may comprise a button that is moved generally linearly in relation to the housing of the device such as a sliding button.

These and other aspects of and advantages with the present invention will become apparent from the following detailed description of the invention and from the accompanying drawings.

BRIEF DESCRIPTION OF THE DRAWINGS

In the following detailed description of the invention, reference will be made to the accompanying drawings, of which

DETAILED DESCRIPTION OF THE INVENTION

In the present application, when the term "distal part/end" is used, this refers to the part/end of the injection device, or the parts/ends of the members thereof, which under use of the injection device is located the furthest away from the medicament injection site of the patient. Correspondingly, when the term "proximal part/end" is used, this refers to the part/end of the injection device, or the parts/ends of the members thereof, which under use of the injection device is located closest to the medicament injection site of the patient.

Figure 1:
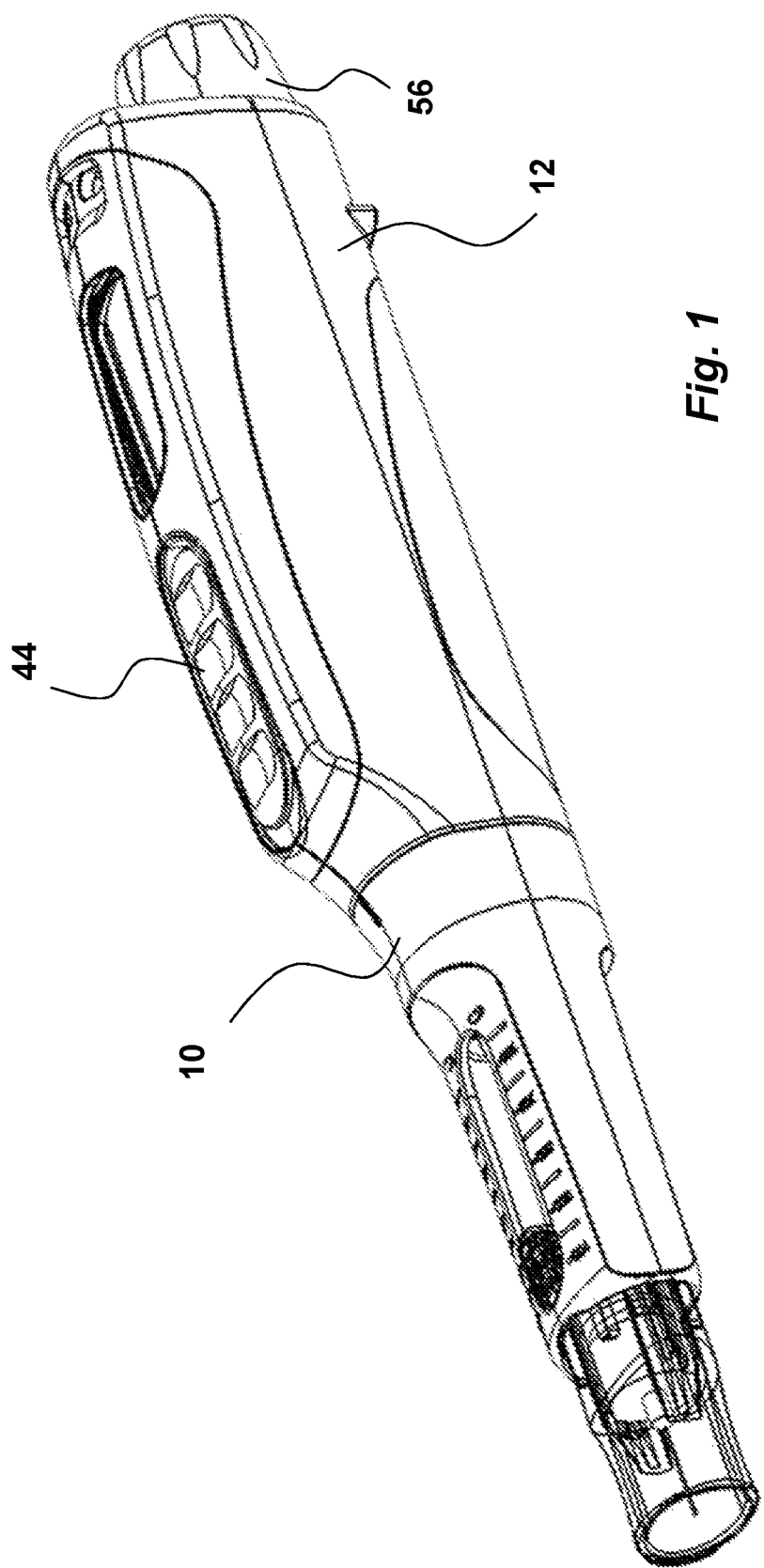
FIG. 1 is a perspective view of a medicament delivery device that may comprise the present invention.

The device shown in the drawings comprises a proximal housing part 10 and a distal housing part 12, FIG. 1. The proximal housing part 10 is arranged and designed to accommodate a medicament container 14, FIG. 2. The proximal end of the medicament container 14 is arranged to fit into a neck 16, FIG. 2, at the proximal end of the proximal housing part 10. A medicament delivery member 17, such as an injection needle, a nasal or mouth piece, a nozzle or the like, may be adapted to be connected to the neck 16 for delivering a dose of medicament. The connection may comprise a number of attachment members such as threads, bayonet connections, luer-locks, just to mention a few.

Figure 2:
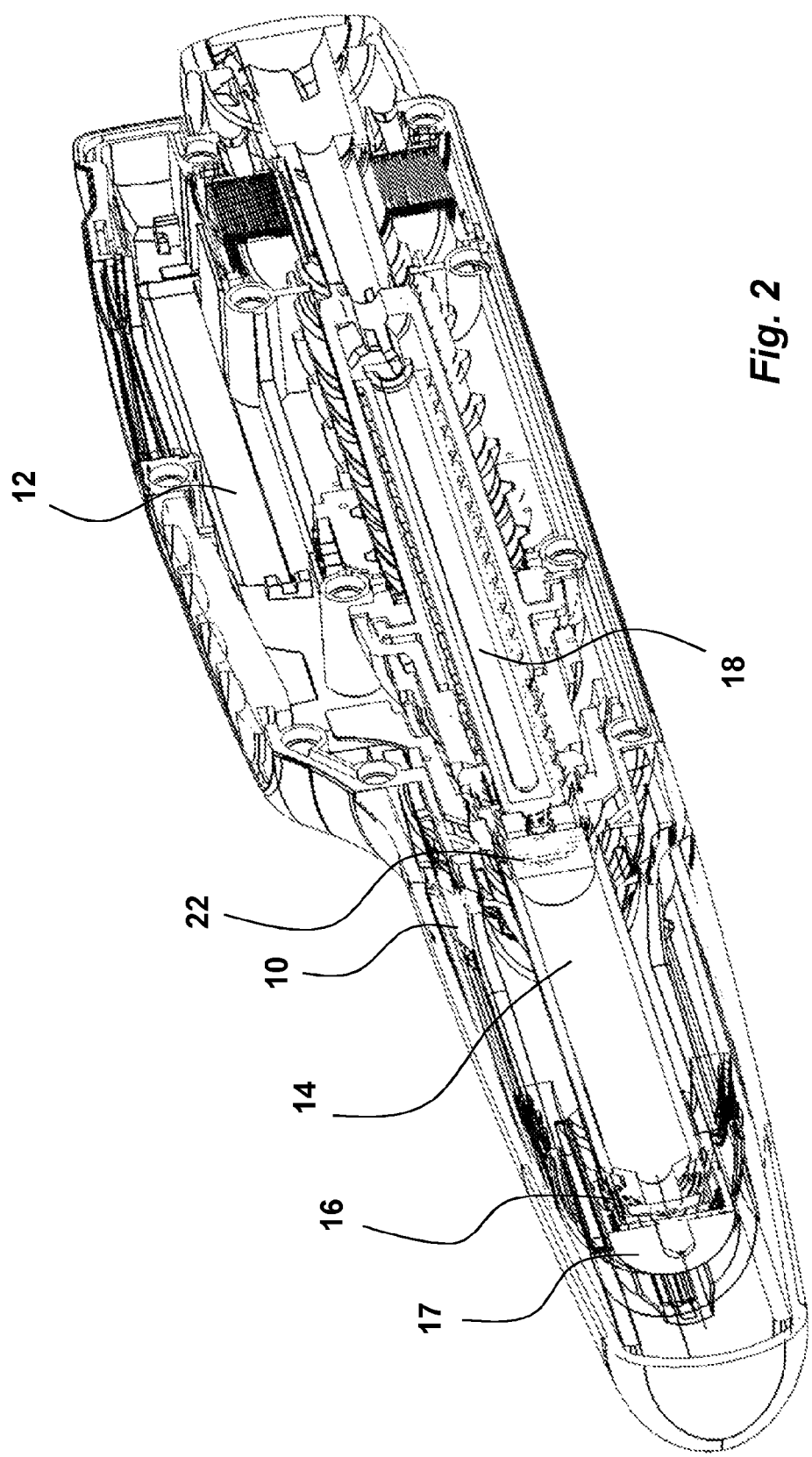
FIG. 2 is a cross-sectional side view of the embodiment of FIG. 1.
Figure 3:
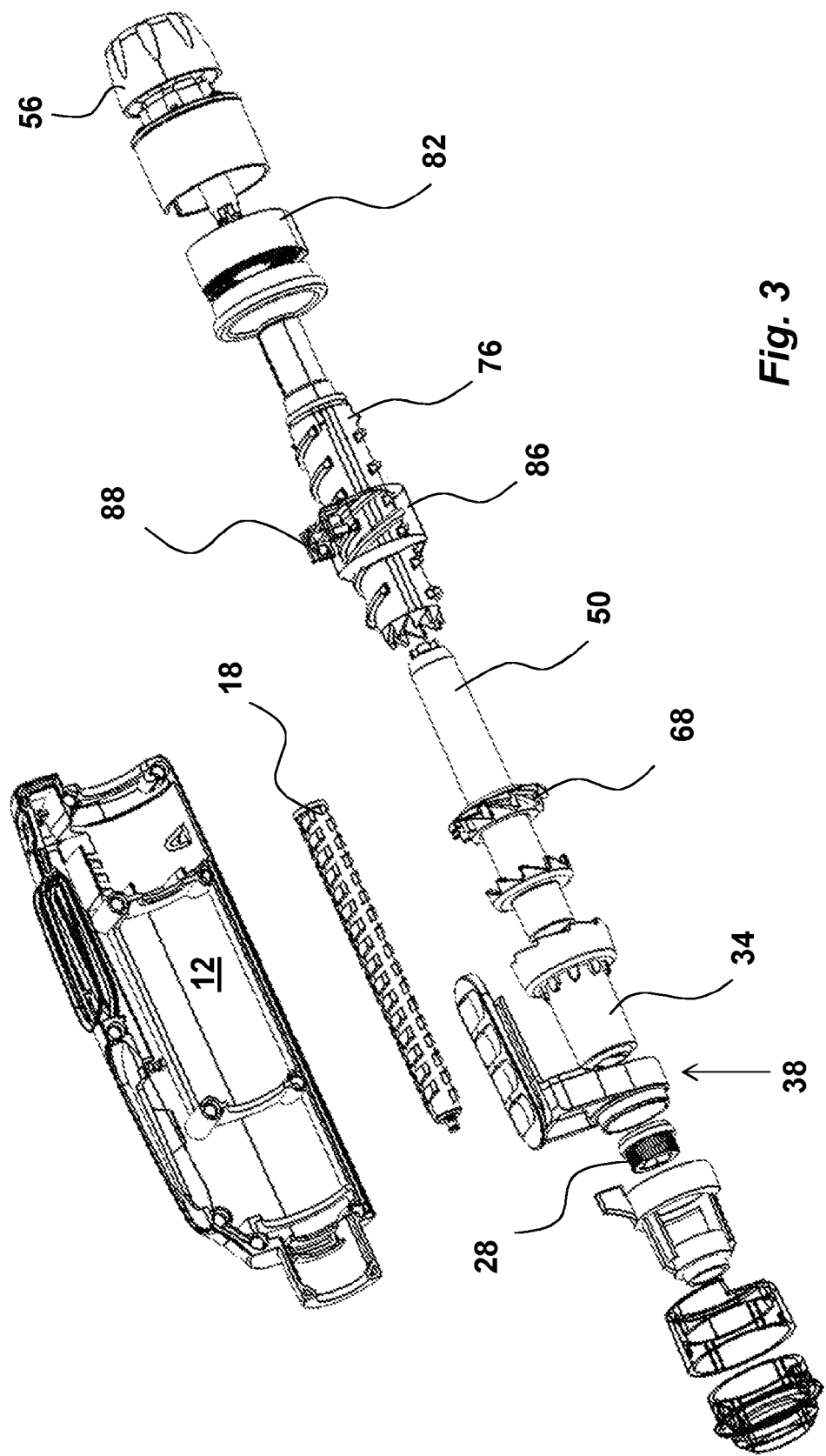
FIG. 3 is an exploded view of the device of FIG. 1.
Figure 5:
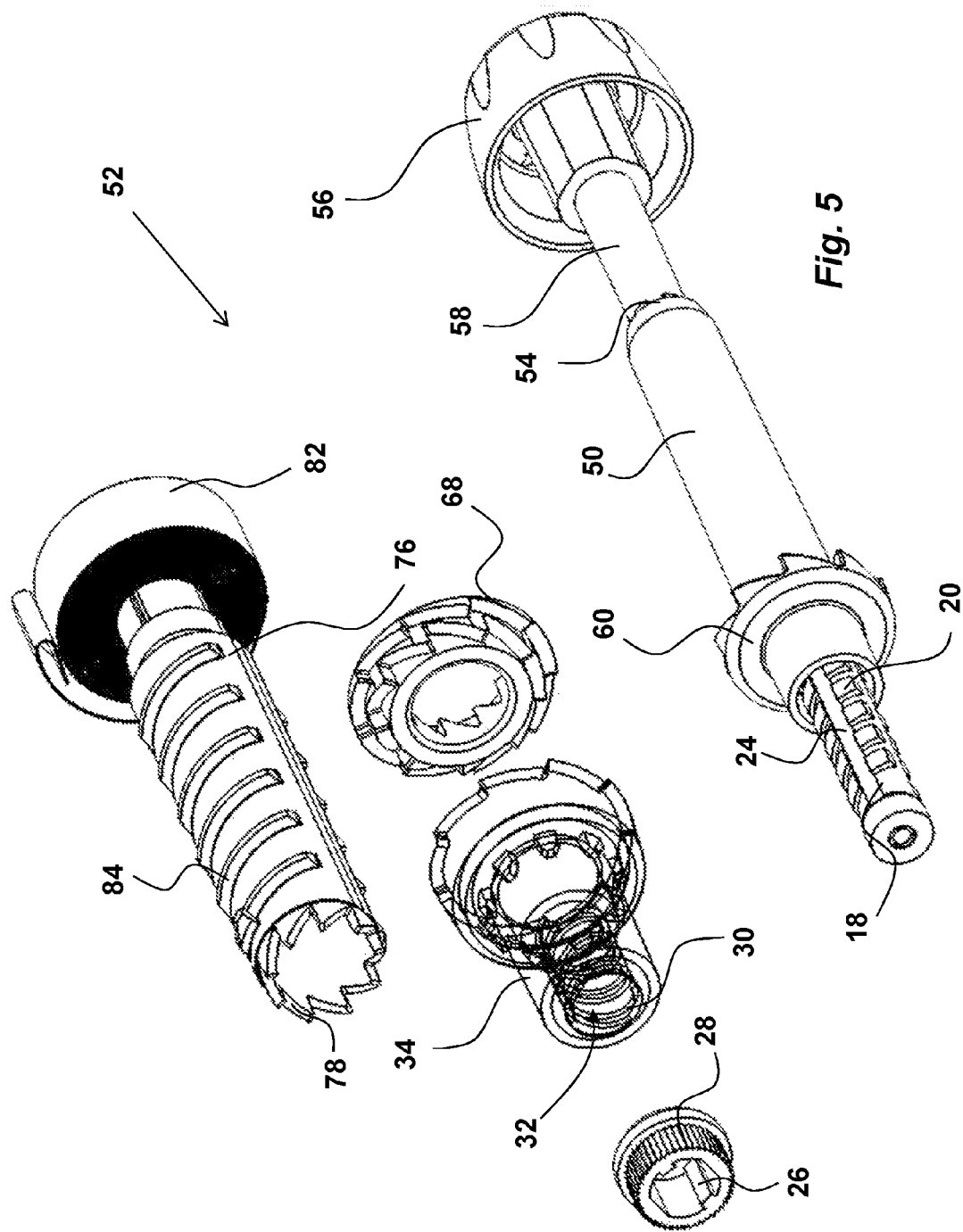
FIG. 5 is an exploded view of a dose and drive setting mechanism comprised in the device of FIG. 1.

An elongated plunger rod 18, FIG. 3, is provided with threads 20, FIG. 5, on its outer surface and having a proximal end in contact with a stopper 22, FIG. 2, movably arranged inside the medicament container 14. The plunger rod 18 is further provided with longitudinally extending grooves 24, FIG. 5, which are arranged to cooperate with radially inwardly extending ledges 26 on a guide member 28 arranged fixed to the housing. The guide member could either be an integral part of the housing or a component that is locked or held stationary in relation to the housing.

The threaded plunger rod 18 is cooperating with corresponding threads 30 arranged in a central passage 32 of a generally cylindrically shaped drive nut 34, FIG. 5. The drive nut 34 is arranged with a number of longitudinally directed ledges 36, which ledges 36 are comprised in an activation mechanism 38, FIG. 4.

Figure 4:
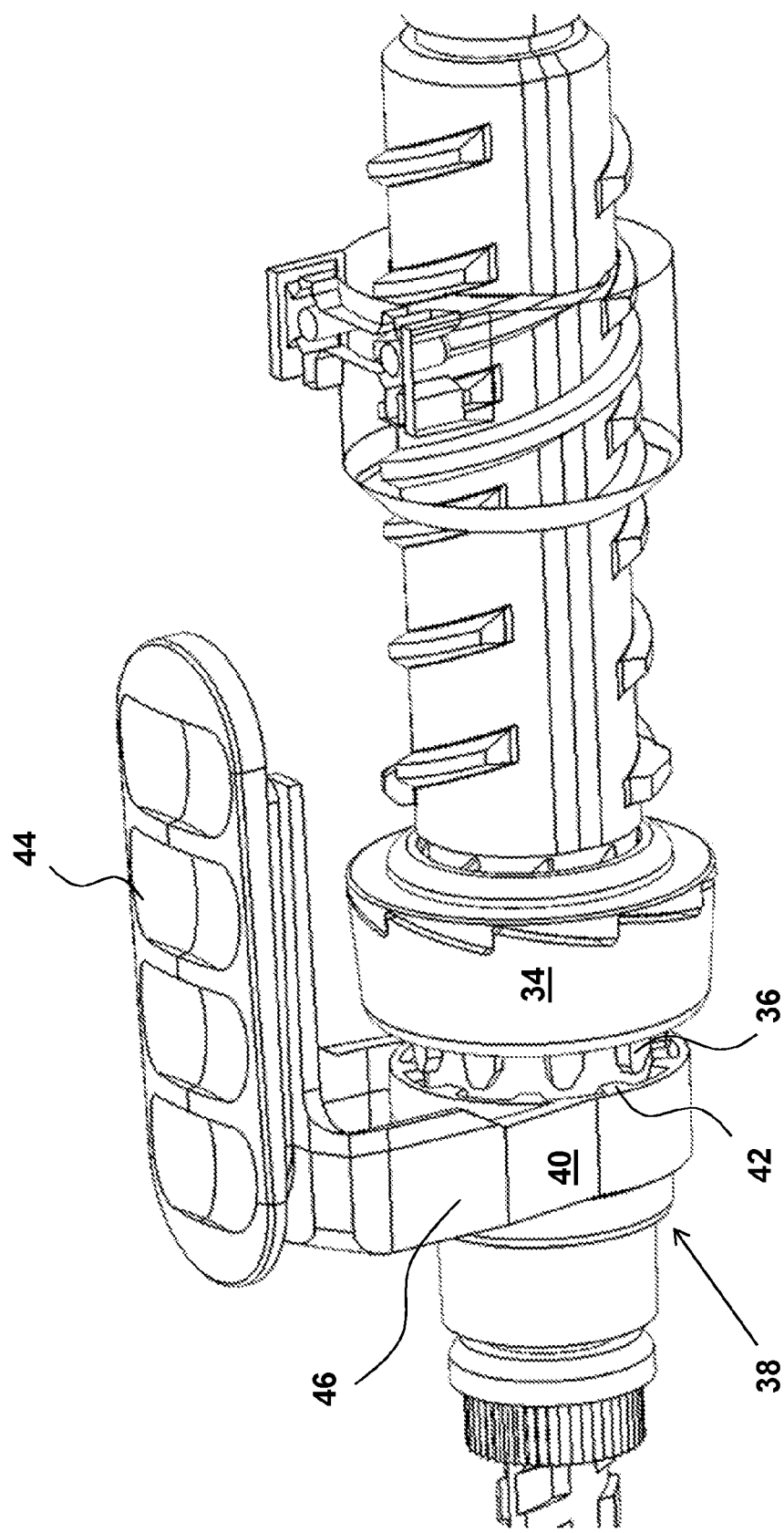
FIG. 4 is a detailed view of the dose and drive setting mechanism.

The activation mechanism 38 further comprises a generally tubularly shaped lock and release member 40, FIG. 4, through which the drive nut 34 extends and provided with corresponding ledges 42 on an inwardly facing surface, which ledges are arranged to cooperate with the ledges 36 of the drive nut 34 to rotationally lock the drive nut 34 in relation to the lock and release member 40. Further the activation mechanism 38 comprises an activation member 44 in the form of a plate arranged slidable on the outer surface of the distal housing part 12. A support 46, FIG. 4, is attached to the activation member 44, extending through an opening in the housing and being attached to the lock and release member 40.

Figure 6:
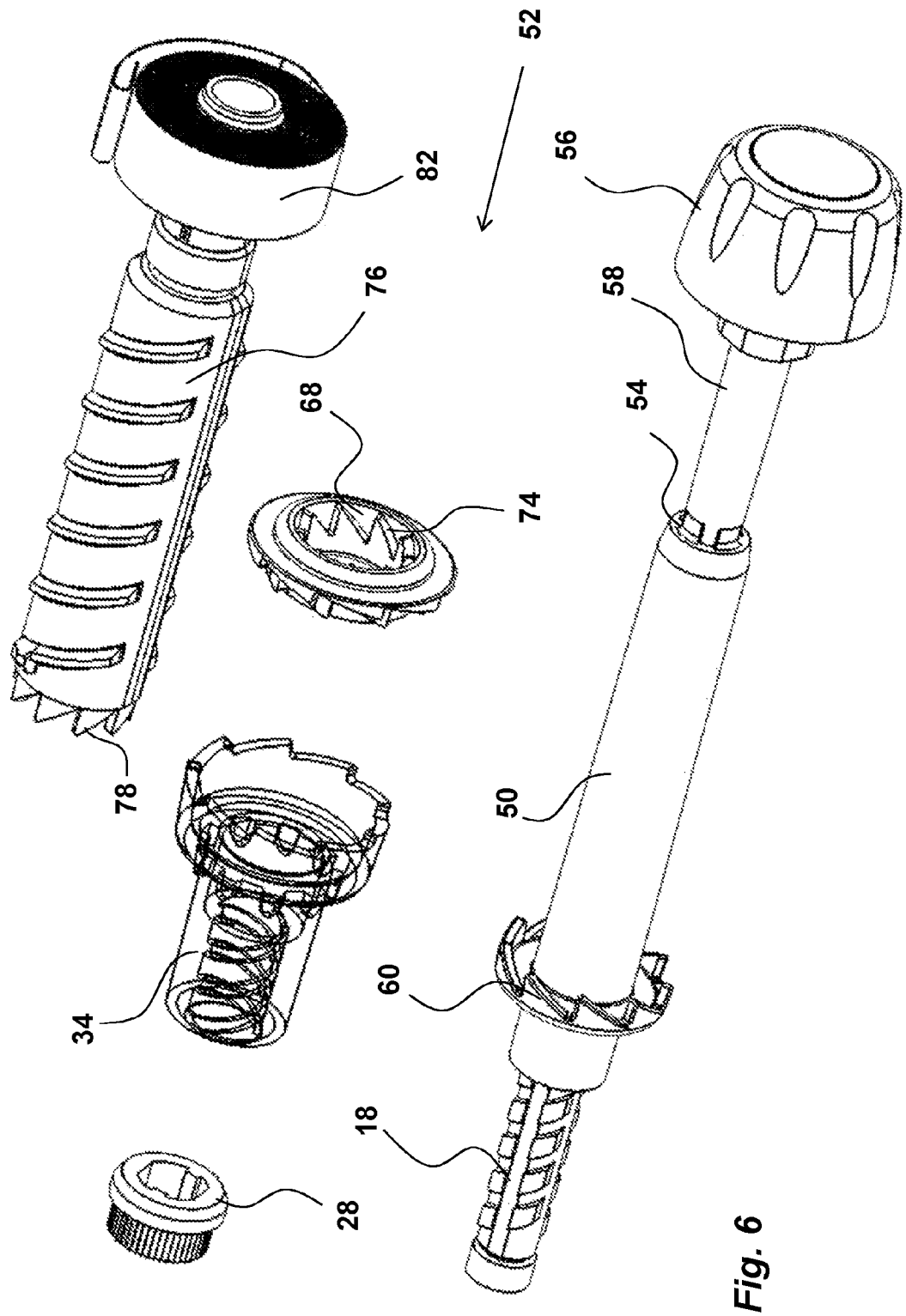
FIG. 6 is an exploded view corresponding to FIG. 5 but turned 180°.
Figure 7:
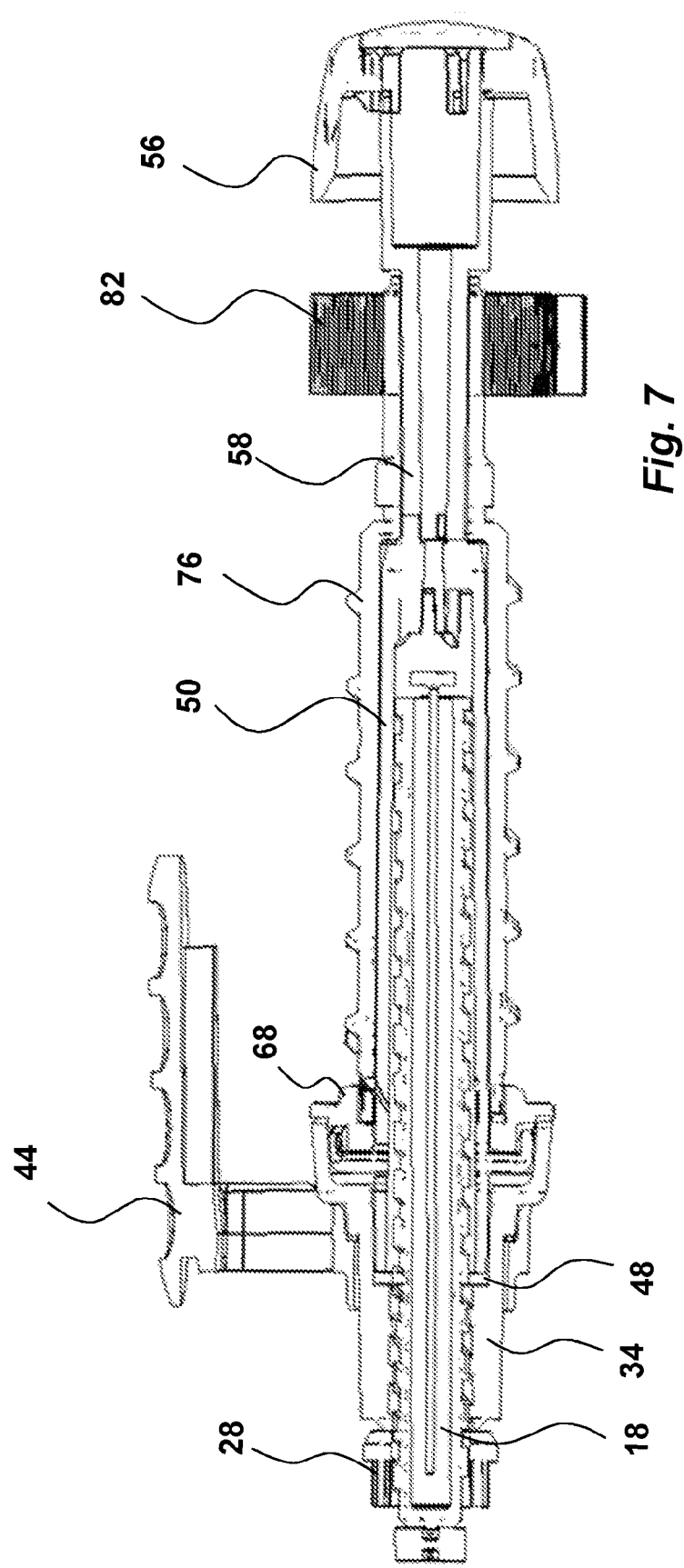
FIG. 7 is a detailed cross-sectional view of the dose and drive setting mechanism of FIG. 5.

A distal part of the drive nut 34 is arranged with a central tubular recess 48, FIG. 7, into which a dose setting sleeve 50 of a dose and drive setting mechanism 52 is arranged, shown in FIGS. 5 and 6. The dose setting sleeve 50 comprises a generally tubular body having a proximal end part fitting into the recess 48 of the drive nut 34, whereby the plunger rod 18 is positioned inside, and extending through, the dose setting sleeve 50. A distal end of the dose setting sleeve 50 is arranged with an attachment post 54.

The dose and drive setting mechanism 52 is further arranged with a dose setting member 56, FIGS. 5 and 6, in the form of a knob rotatably arranged at the distal end of the distal housing part 12 and accessible by a user. The dose setting member 56 is provided with an elongated shaft 58, FIGS. 5 and 6, extending in the proximal direction, where the proximal end of the shaft 58 is arranged with an attachment member of corresponding configuration of the attachment post 54 of the dose setting sleeve 50 so as to connect the two, whereby, when a user rotates the dose setting member 56, so does the dose setting sleeve 50, as will be described below.

Further the dose setting sleeve 50 is arranged with a generally cup-shaped member 60, FIGS. 5 and 6, attached to or made integral with, the dose setting sleeve 50, and where the edge of the cup-shaped member 60 is facing a distal direction. The edge of the cup-shaped member 60 is further arranged with a number of wedge-shaped teeth 62, FIG. 8, of a first unidirectional connection comprising a first ratchet connection, where the distal surfaces of the teeth 62 have an inclination α, FIG. 8, in relation to a plane normal to the longitudinal direction of the device. The teeth also have a certain height $h_1$, FIG. 8.

Figure 8:
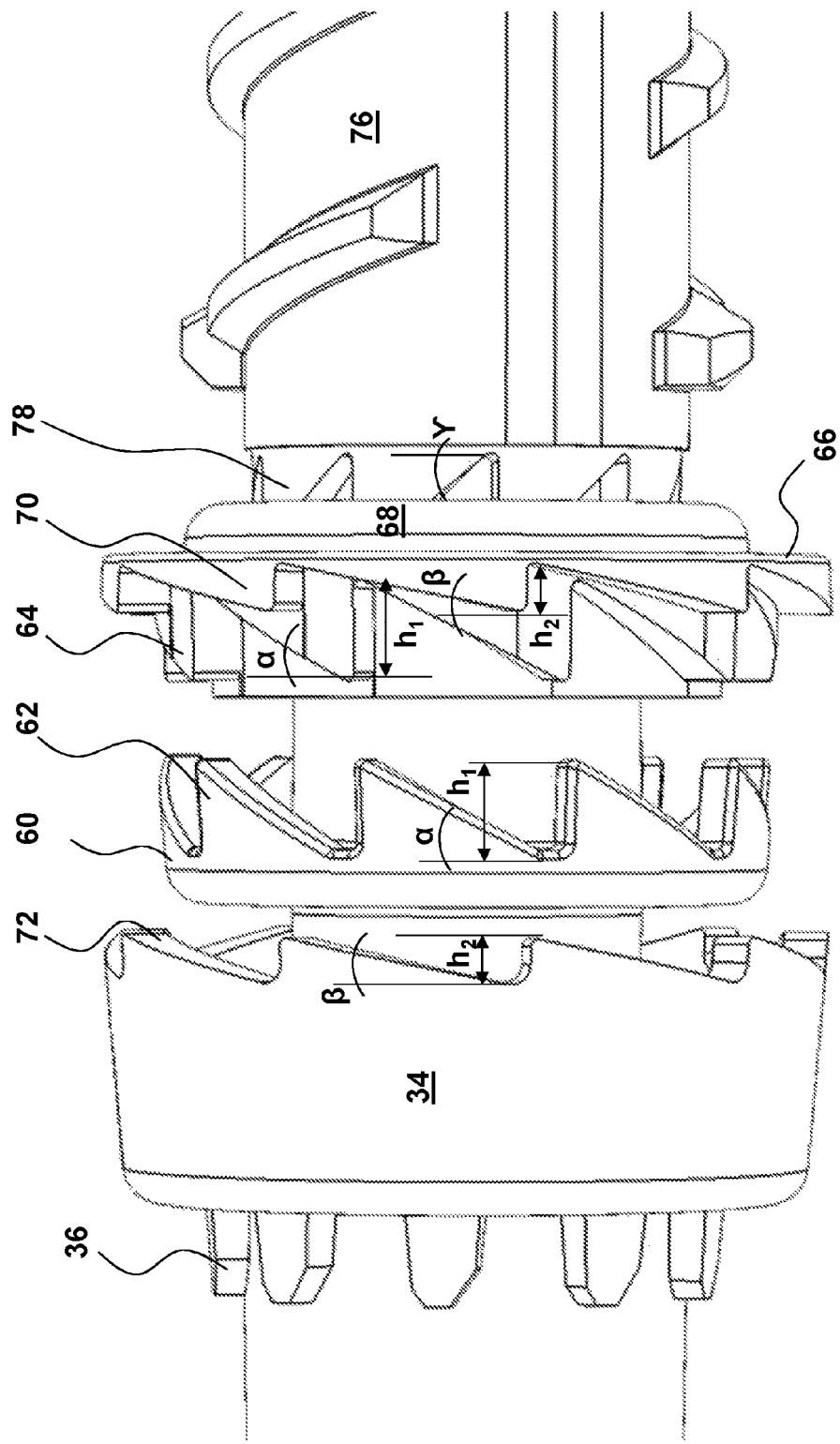
FIG. 8 is a detailed view of first and second ratchet connections comprised in the present invention.

The first ratchet connection further comprises a set of circumferentially extending wedge-shaped teeth 64 arranged on a proximally directed ledge surface of a circumferential ledge 66 of an intermediate member 68, FIG. 8, comprised in the dose and drive setting mechanism 52, FIGS. 5 and 6. The set of wedge-shaped teeth 64 have the same number of teeth, the same inclination α and the same height $h_1$ as the teeth 62 of the cup-shaped member 60 of the dose setting sleeve 50, whereby they cooperate with each other as will be described.

The intermediate member 68 is arranged with a central passage with a diameter somewhat larger than the outer diameter of the dose setting sleeve 50, whereby the latter passes through the intermediate member 68. On the ledge 66 of the intermediate member 68 and outside of the set of teeth 64 of the first ratchet connection as seen in the radial direction is a second set of wedge-shaped teeth 70 of a second ratchet connection, FIG. 8, which second set of wedge-shaped teeth 70 have a certain number of teeth, a certain inclination β in relation to a plane normal to the longitudinal direction of the device and a certain tooth height $h_2$, FIG. 8.

The second set of teeth 70 cooperate with a set of teeth 72 on a distally directed surface of the drive nut 34, FIG. 8, having the same inclination β and tooth height $h_2$, whereby they cooperate with each other as will be described.

Figure 9:
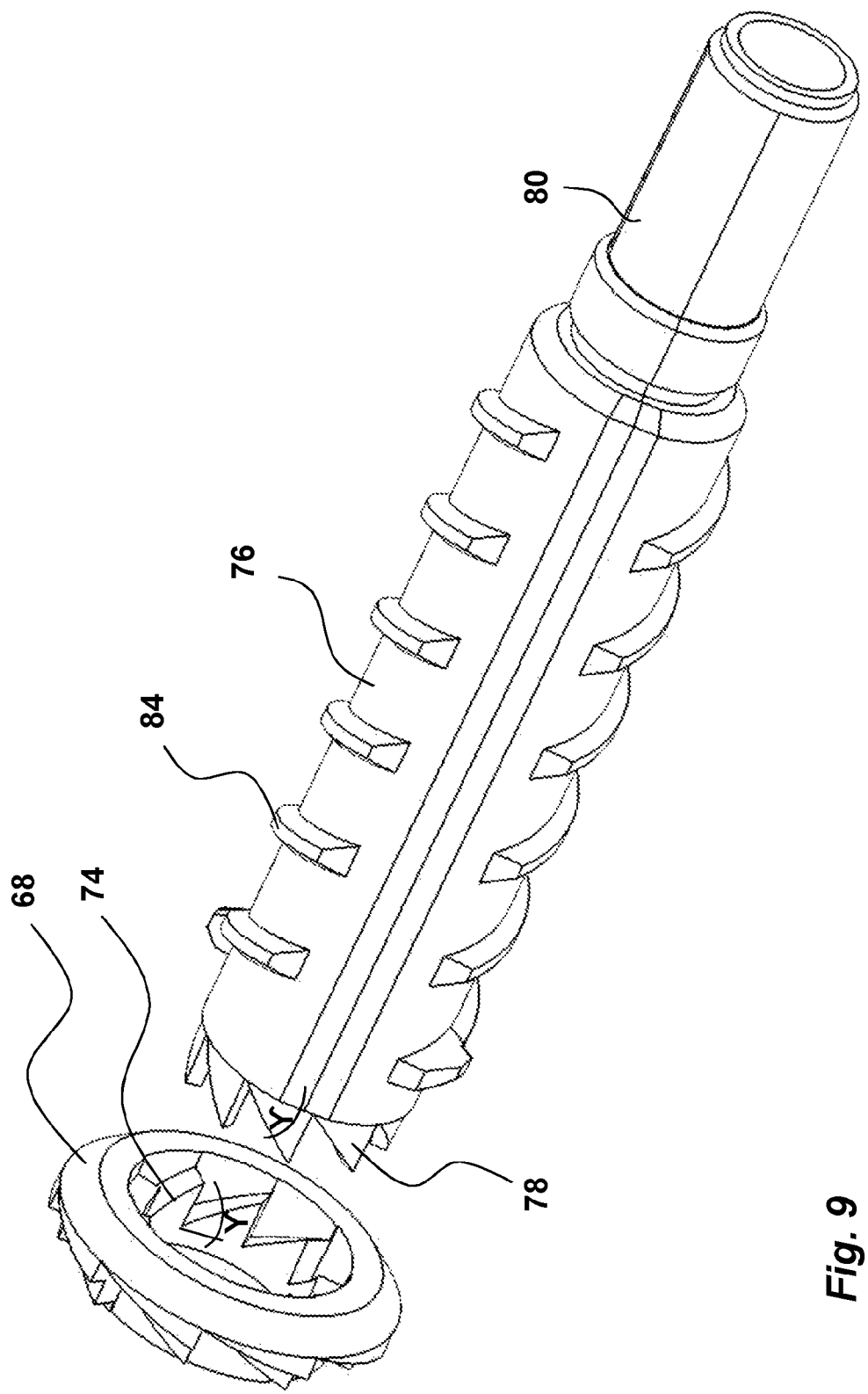
FIG. 9 is a detailed exploded view of components comprised in the present invention

A distally directed ledge surface of the intermediate member 68 is further arranged with a distally directed circumferential set of wedge-shaped teeth 74 comprised in a third connection, FIG. 9, having an inclination γ in relation to a plane normal to the longitudinal direction of the device. Further, the dose and drive setting mechanism 52 comprises a dose drive sleeve 76, FIGS. 5, 6, 9, having a generally tubular shape and being positioned coaxially outside and surrounding the dose setting sleeve 50 as seen in the radial direction, where the dose drive sleeve 76 is rotatable in relation to the dose setting sleeve 50. The dose drive sleeve 76 is provided with a proximally directed end surface, which surface is provided with circumferential set of wedge-shaped teeth 78, FIG. 9, which set of wedge-shaped teeth 78 have the same number of teeth and the same inclination γ as the distally directed teeth 74 of the intermediate member 68, whereby they cooperate with each other as will be described.

The dose drive sleeve 76 is further arranged with an attachment member 80 at a distal end thereof, FIG. 9. A spring force member 82, FIGS. 5 and 6, shown in the form of a clock spring, is attached with an inner end to the attachment member 80 of the dose drive sleeve 76. An outer end of the spring force member 82 is attached to a point fixed in relation to the distal housing part 12 of the device.

Figure 10:
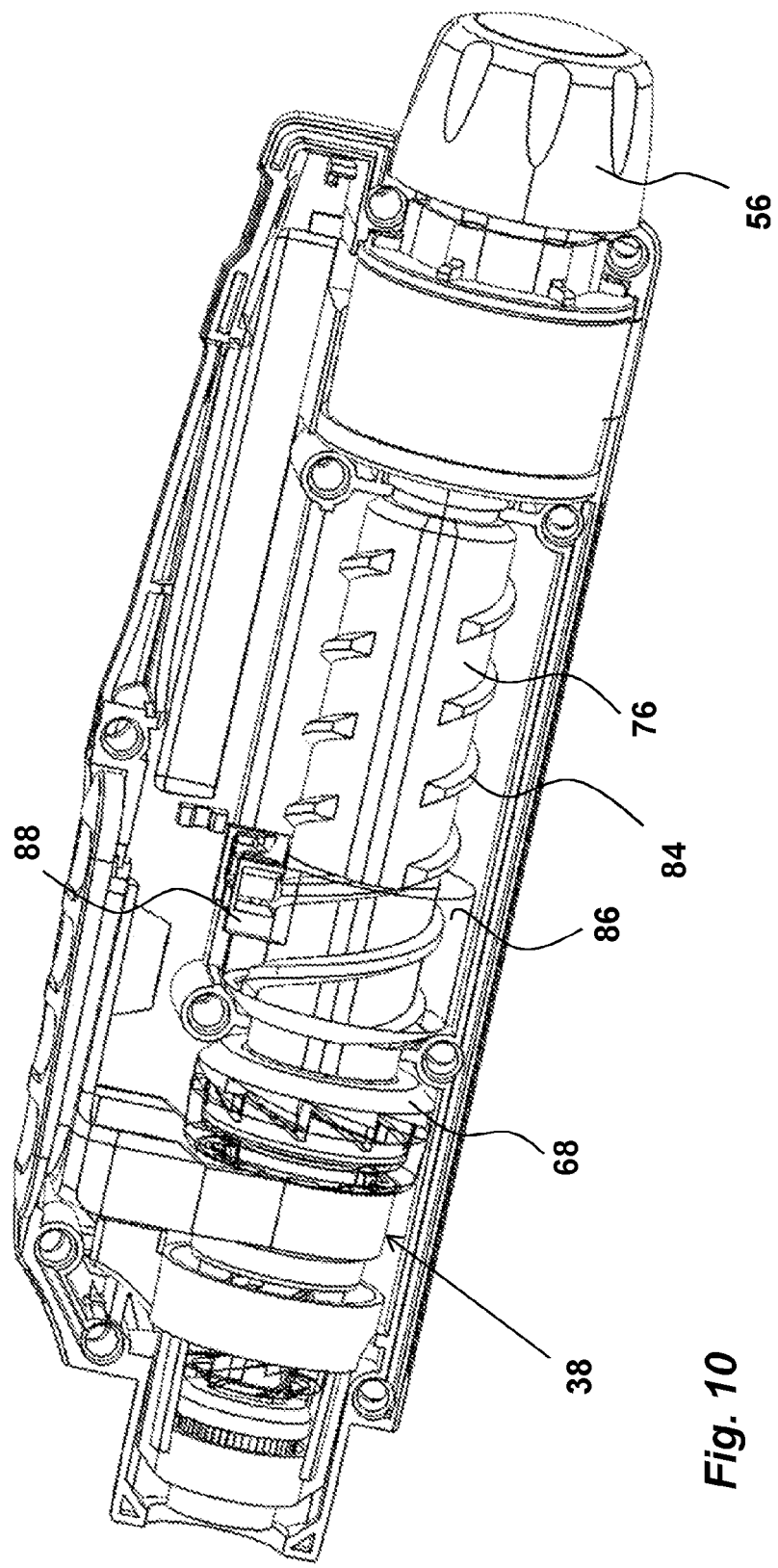
FIG. 10 is a detailed view of the dose and drive setting mechanism.

The dose drive sleeve 76 is further arranged with thread segments 84, FIG. 10, on its outer surface, which thread segments 84 cooperate with internal threads on a dose indication nut 86, such that rotation of the dose drive sleeve 76 causes the dose indication nut 86 to move linearly in the longitudinal direction of the device. The dose indication nut 86 is further provided with attachment means 88, FIG. 10, for attaching suitably position sensor (not shown), which position sensors are arranged to cooperate with corresponding indicators positioned on e.g. a printed circuit board (not shown).

The device is intended to function as follows.

Dose Setting

When the user is to take a dose of medicament from the device a preferred and prescribed dose size is to be set. The user then activates the dose and drive setting mechanism 52, whereby he/she turns the dose setting member 56, whereby its shaft 58 also is turned, and due to the connection with the dose setting sleeve 50, the latter is also turned. Because the cup-shaped member 60 is attached or integral to the dose setting sleeve 50, it is also turned. The configuration of the wedge-shaped teeth 62 of the cup-shaped member 60 and the wedge-shaped teeth 64 of the intermediate member 68 of the first ratchet connection causes the intermediate member 68 to be brought along and rotated together with the dose setting sleeve 50.

Figure 11:
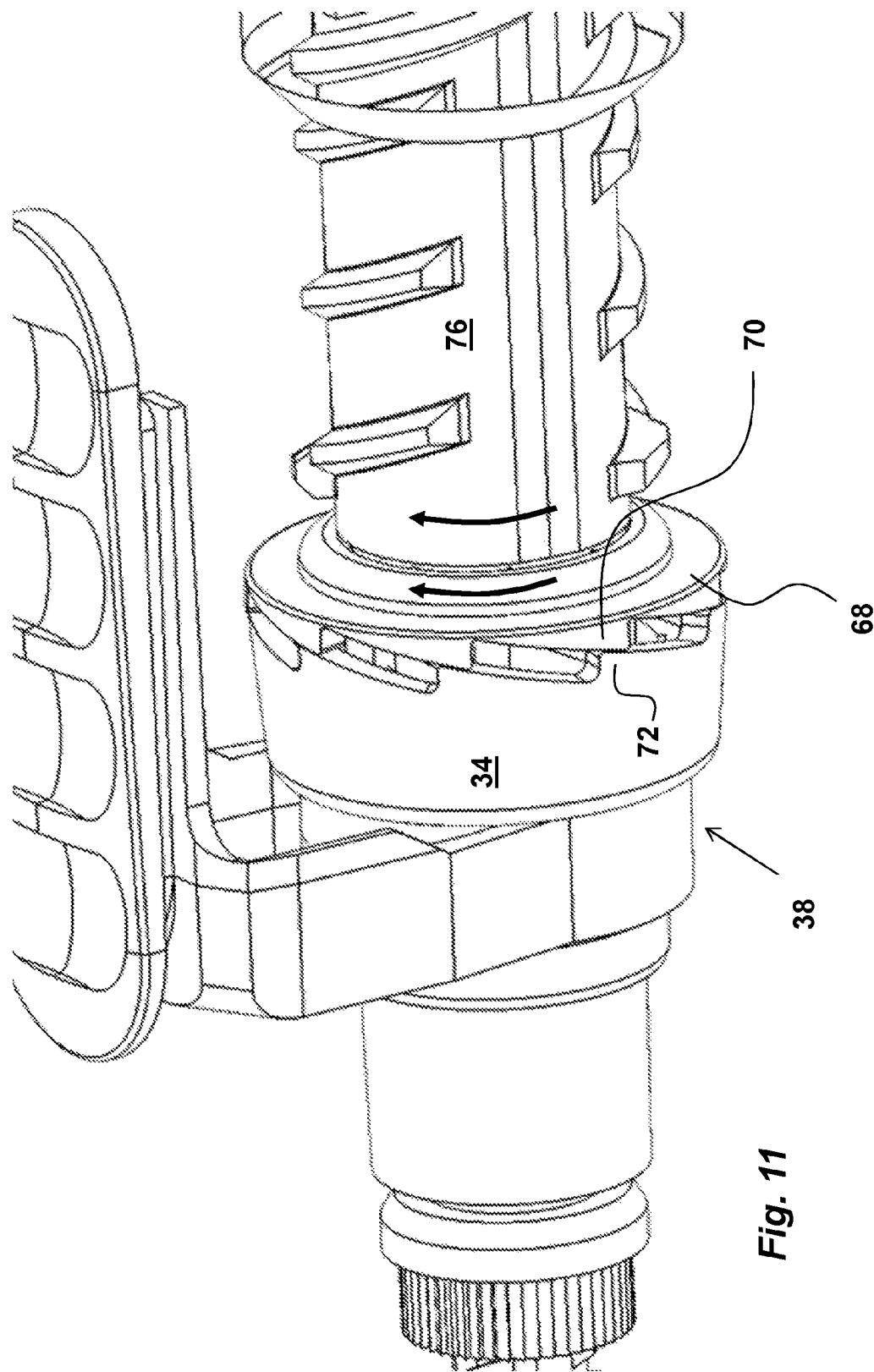
FIGS. 11 to 13 show detailed views of different functional states of the present invention, and FIGS. 14*a* and *b* show detailed views of interaction between two components comprised in the dose setting mechanism of FIG. 10.
Figure 14B:
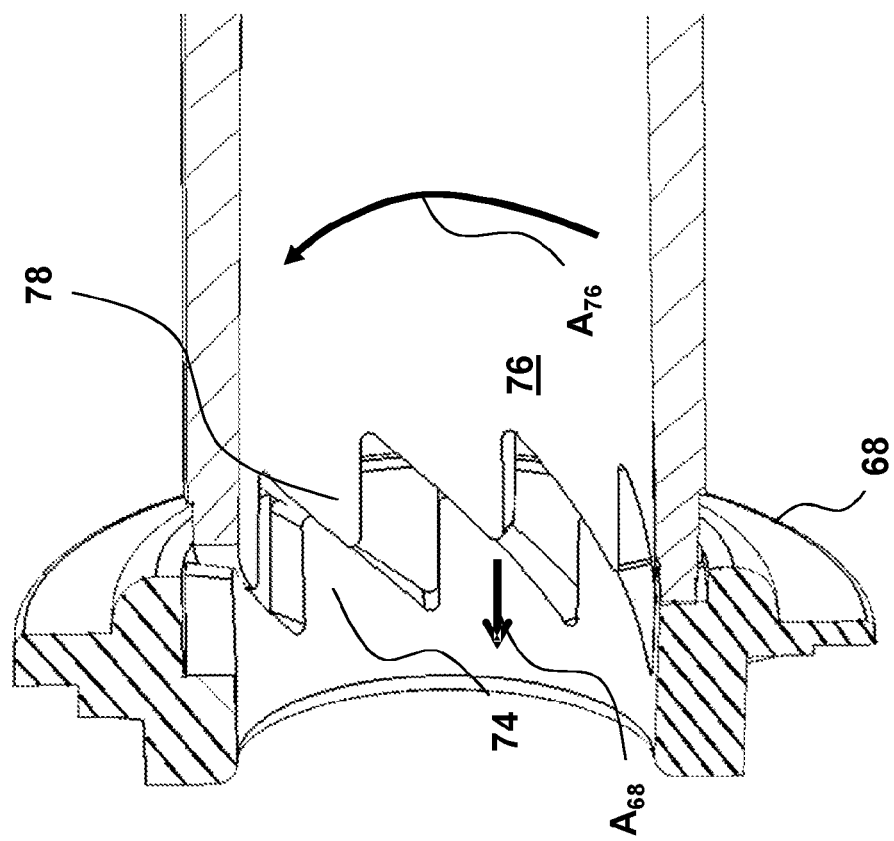

Further, the distally directed teeth 74 of the intermediate member 68 are configured such with the teeth 78 of the dose drive sleeve 76 that the dose drive sleeve 76 is brought along and rotated when the intermediate member 68 is rotated. Because the inner end of the spring force member 82 is attached to the dose drive sleeve 76, the spring force member 82 will now be tensioned when the dose drive sleeve 76 is rotated. Also, during the turning of the intermediate member 68, the second set of proximal teeth 70 of the second ratchet connection are configured such in relation to the cooperating teeth 72 of the drive nut 34 such that the inclined surfaces of the teeth slide in relation to each other in this direction, FIG. 11, because the drive nut 34 is locked due to the interconnection between its ledges 36 and the ledges 42 of the lock and release member 40 of the activation mechanism 38, FIG. 11. However, the intermediate member 68 is prevented from being rotated back due to the configuration of the wedge-shaped teeth of the second ratchet connection. Thus the spring force member 82 is held tensioned by the dose and drive setting mechanism 52 after operation of the dose setting member 56. Further, the intermediate member 68 is forced in the proximal direction as indicated by arrow A68 of FIG. 14b, ensuring a safe connection between the intermediate member 68 and the drive nut 34 due to the force from the spring member acting to turn the dose drive sleeve 76 as indicated by arrow A76, FIG. 14b, providing a force F76 on the third connection between the proximally directed teeth 78 of the dose drive sleeve 76 acting with its inclined surfaces on the inclined surfaces of the distally directed teeth 74 of the intermediate member 68.

Further the turning of the dose drive sleeve 76 causes the dose indication nut 86 to move linearly in the longitudinal direction of the device due to the threaded connection between the dose drive sleeve 76 and the dose indication nut 86. The sensors will then move along the indicators, whereby information may be obtained as how far the dose indication nut has moved, which distance corresponds to a certain dose of medicament to be delivered. This certain dose may be displayed to the user in any appropriate way known to the person skilled in the art.

Dose Delivery

Figure 12:
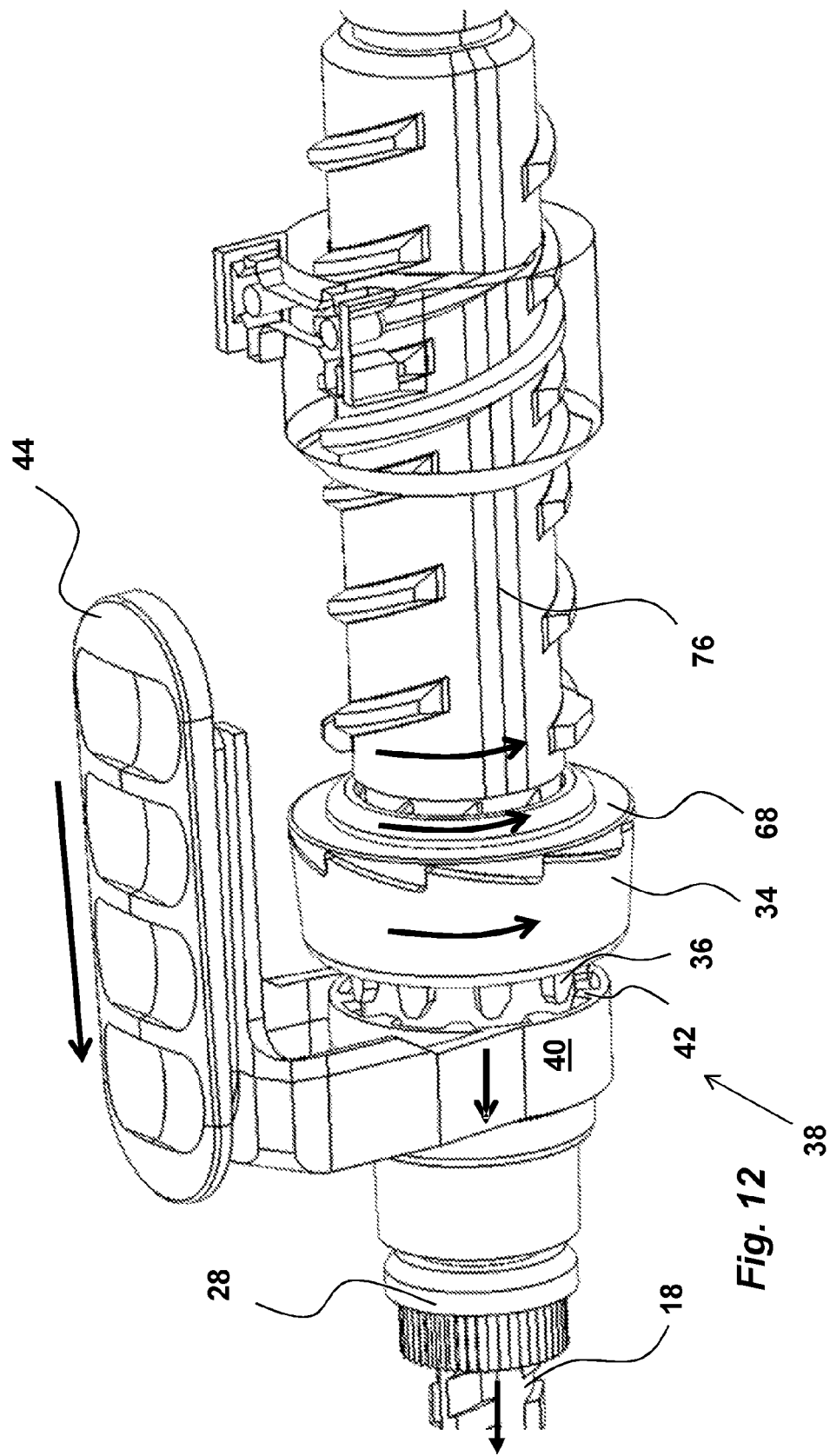

The device is now ready to deliver a dose of medicament. The user then operates the dose activation mechanism 38. This is done by sliding the activation button 44 in the longitudinal direction in relation to the housing, FIG. 12. This causes the ledges 42 of the lock and release member 40 to be moved out of contact with the ledges 36 of the drive nut 34, FIG. 8, whereby the latter is free. The connection of the second ratchet connection with the wedge-shaped teeth 72 of the drive nut 34 and the teeth 70 of the intermediate member 68 are arranged such that the intermediate member 68 will rotate the drive nut 34, FIG. 12, this in turn due to the connection between the distally directed wedge-shaped teeth 74 of the intermediate member 68 cooperating with the teeth 78 of the dose drive sleeve 76 and since the spring force member 82 is tensioned and acting on the dose drive sleeve 76, the spring will force the dose drive sleeve 76 to rotate. Thus, the drive nut 34 will rotate by the force of the spring force member 82 and due to the threaded connection between the drive nut 34 and the plunger rod 18, the latter will be moved in the proximal direction linearly due to the ledges 26 of the guide member 28 fitting into the longitudinal grooves 24 of the plunger rod 18, thereby preventing rotation of the plunger rod 18. The movement of the plunger rod 18 in the longitudinal direction will cause the stopper of the medicament container 14 to be moved in the proximal direction, whereby a dose of medicament will be delivered.

Resetting of a Set Dose

If the user for some reason wishes to reduce the set dose, either if set too high or the device should be reset to zero, the user activates the dose and drive setting mechanism 34 by turning the dose setting member 56 in the opposite direction as to the setting direction. This will then cause the dose setting sleeve 50 to rotate and thus also the cup-shaped member 60 indicated by arrow I in FIG. 13.

The drive nut 34 has been moved to the left in the figure for clarity. The actual position of the drive nut is indicated by broken lines with reference numeral 34'.

Figure 13:
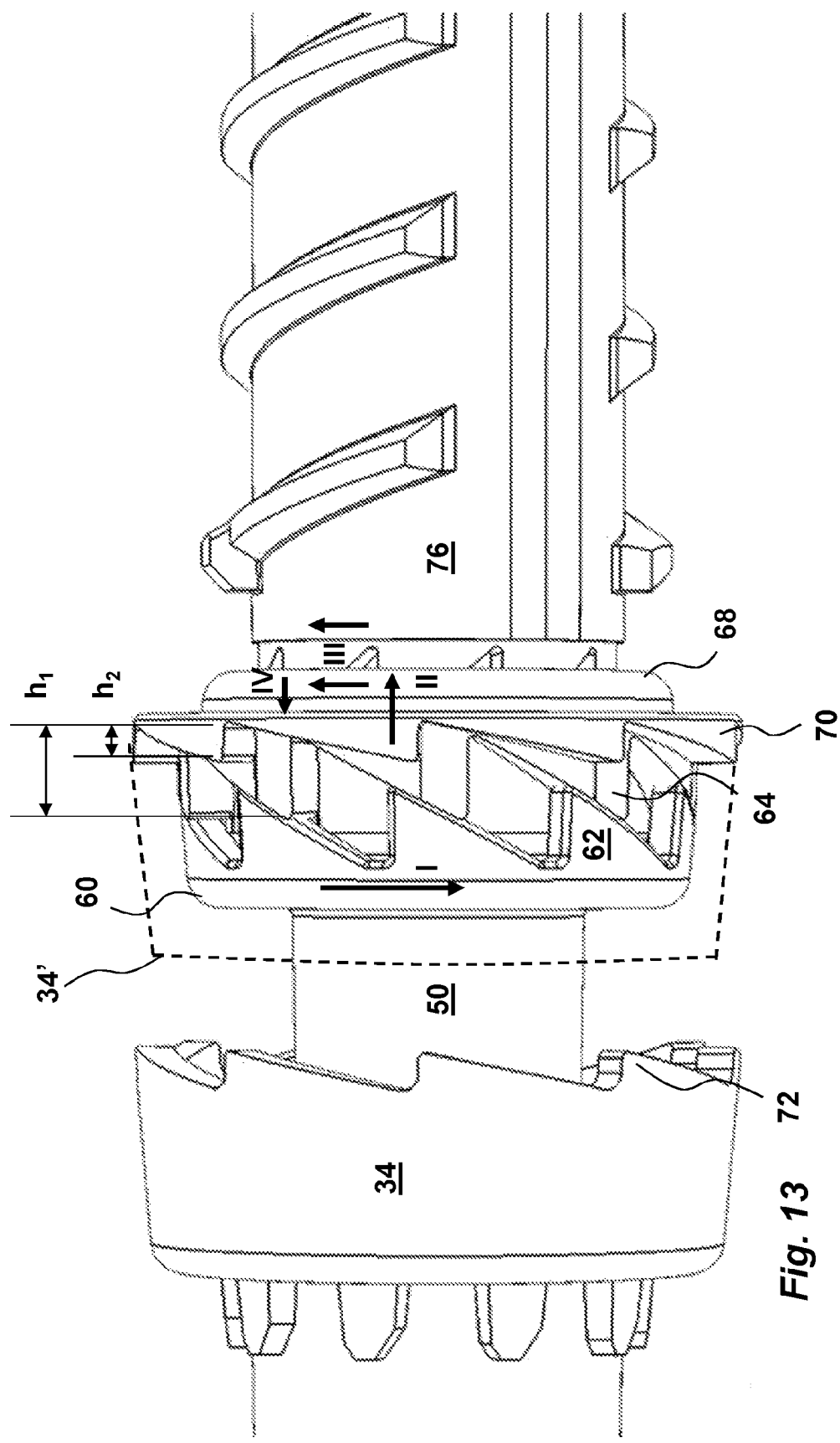
Figure 14A:
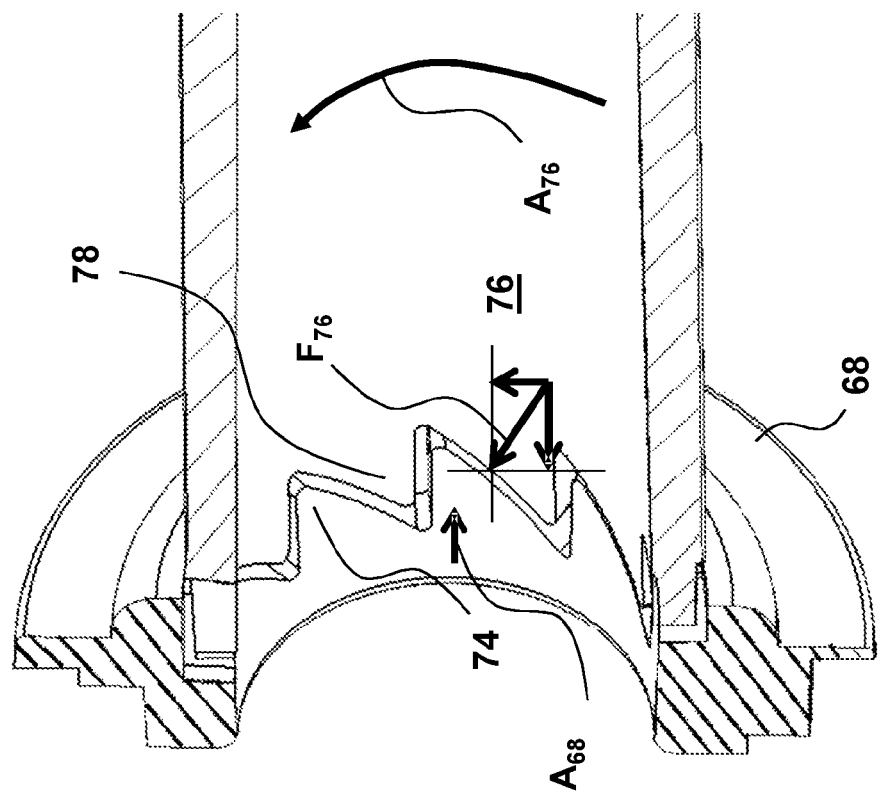

The teeth 62 of the first ratchet connection on the cup-shaped member 60 will now slide with their inclined surfaces on the inclined surfaces of the teeth 64 of the intermediate member 68, FIG. 13. This action will cause the intermediate member 68 to be moved in the distal direction indicated by arrow II in FIG. 13. The movement of the intermediate member 68, as also indicated by arrow A68 in FIG. 14a, is facilitated by the third connection, where the inclined surfaces of the distally directed teeth 74 slide on the inclined surfaces of the teeth 78 of the dose drive sleeve 76. The movement of the intermediate member is done against the force F, FIG. 14a, from the spring force member 82, also turning the intermediate member 68 somewhat.

The movement of the intermediate member 68 in the distal direction will cause it to be moved also in relation to the drive nut 34, which is held fixed by the activation mechanism 38. Due to the difference in inclination and also in height of the teeth on the intermediate member 68, the teeth 72 of the drive nut 34 and the cooperating teeth 70 of the intermediate member 68 of the second ratchet connection, having a lesser inclination $\beta$ and lesser height h2, will be moved out of contact with each other during the movement of the intermediate member 68 due to the interaction between the teeth 62 of the cup-shaped member 60 of the dose setting sleeve 50 and the teeth 64 of the intermediate member 68 of the first ratchet connection, having a larger inclination $\alpha$ and larger height h1.

When the teeth of the second ratchet connection are moved out of contact with each other, the intermediate member 68 and the dose drive sleeve 76 are free to rotate due to the force from the spring force member 82 on the dose drive sleeve 76 indicated by arrow III in FIG. 13, so as to reduce the tension of the spring force member 82. However, due to the interaction between the distally directed teeth 74 of the intermediate member 68 and the teeth 78 of the dose drive sleeve 76 of the third connection, the intermediate member 68 is forced in the proximal direction again, as indicated by arrow IV and also by arrow A68 in FIG. 14b, whereby the teeth of the second ratchet connection are again moved in contact with each other, locking the intermediate member 68 from rotation. In order to reduce the dose size further and thereby reduce the tension of the spring force member 82, the user again has to perform the above mentioned turning of the dose setting member 56. Thus for each operation by a user, the dose is reduced one increment.

It is to be understood that the embodiments described above and shown in the drawings are to be regarded only as non-limiting examples of the invention and that it may be modified in a number of ways within the scope of the patent claims.

The invention claimed is:

1. A medicament delivery device, comprising:
    a housing configured to accommodate a medicament container;
    a plunger rod;
    a drive member configured to interact with the plunger rod for moving the plunger rod in a proximal direction for expelling a dose of medicament from the medicament container; and
    a dose and drive setting mechanism, comprising:
        a dose setting assembly operably connected to a force member such that setting a dose energizes the force member, wherein the dose setting assembly comprises a dose setting member, a dose setting sleeve fixedly connected to the dose setting member, and a dose drive sleeve coaxially arranged on the dose setting sleeve and operably connected to the force member; and
        an intermediate member configured to interact with the dose setting assembly and the drive member for setting and re-setting a dose, wherein the intermediate member is configured to interact with the dose setting sleeve through a first unidirectional direct connection, is configured to interact with the drive member through a second unidirectional direct connection, and is configured to interact with the dose drive sleeve through a third direct connection.

2. The medicament delivery device of claim 1, wherein the second unidirectional connection is configured to transmit movement between the force member and the drive member for urging the plunger rod to expel a dose of medicament.

3. The medicament delivery device of claim 1, wherein the first unidirectional connection and the third connection are configured to transmit movement in one direction between the dose setting member and the force member for energizing the force member.

4. The medicament delivery device of claim 3, wherein the second unidirectional connection is configured to transmit movement between the force member and the drive member for urging the plunger rod to expel a dose of medicament.

5. The medicament delivery device of claim 4, wherein the second unidirectional connection is configured to enable movement in the one direction and to prevent movement in an opposite direction so as to hold the force member in an energized state.

6. The medicament delivery device of claim 1, wherein the third connection enables the intermediate member to move in a longitudinal direction for connecting and disconnecting the second unidirectional connection.

7. The medicament delivery device of claim 1, wherein each of the first unidirectional connection and the second unidirectional connection comprises a ratchet connection.

8. The medicament delivery device of claim 7, wherein the ratchet connections comprise wedge-shaped teeth.

9. The medicament delivery device of claim 8, wherein the teeth of a first ratchet connection of the first unidirectional connection have a height that is higher than a height of the teeth of a second ratchet connection of the second unidirectional connection.

10. The medicament delivery device of claim 9, wherein the teeth of the first ratchet connection have an inclination angle that is larger than an inclination angle of the teeth of the second ratchet connection.

11. The medicament delivery device of claim 1, wherein the third connection comprises a ratchet connection with wedge-shaped teeth.

12. The medicament delivery device of claim 1, wherein each of the first unidirectional connection and the second unidirectional connection comprises a ratchet connection, and the third connection comprises a ratchet connection with wedge-shaped teeth.

13. A dose and drive setting mechanism for a medicament delivery device, the dose and drive setting mechanism comprising:
    a dose setting assembly operably connected to a force member such that setting a dose energizes the force member, wherein the dose setting assembly comprises a dose setting member, a dose setting sleeve fixedly connected to the dose setting member, and a dose drive sleeve coaxially arranged on the dose setting sleeve and operably connected to the force member; and
    an intermediate member configured to interact with the dose setting assembly and the medicament delivery device for setting and re-setting a dose, wherein the intermediate member is configured to interact with the dose setting sleeve through a first unidirectional direct connection, is configured to interact with the drive member through a second unidirectional direct connection, and is configured to interact with the dose drive sleeve through a third direct connection.

14. The mechanism of claim 13, wherein the second unidirectional connection is configured to transmit movement between the force member and the drive member for urging the plunger rod to expel a dose of medicament.

15. The mechanism of claim 13, wherein the first unidirectional connection and the third connection are configured to transmit movement in one direction between the dose setting member and the force member for energizing the force member.

16. The mechanism of claim 15, wherein the second unidirectional connection is configured to transmit movement between the force member and the drive member for urging the plunger rod to expel a dose of medicament.

17. The mechanism of claim 16, wherein the second unidirectional connection is configured to enable movement in the one direction and to prevent movement in an opposite direction so as to hold the force member in an energized state.

18. The mechanism of claim 13, wherein the third connection enables the intermediate member to move in a longitudinal direction for connecting and disconnecting the second unidirectional connection.

19. The mechanism of claim 13, wherein at least one of the first and second unidirectional connections and the third connection comprises a ratchet connection.

20. The mechanism of claim 19, wherein the ratchet connections comprise wedge-shaped teeth.

* * * * *